(12) United States Patent
Capuzzi et al.

(10) Patent No.: US 9,409,877 B2
(45) Date of Patent: Aug. 9, 2016

(54) PROCESS FOR THE SYNTHESIS OF 5-HYDROXYMETHYLFURFURAL FROM SACCHARIDES

(71) Applicant: NOVAMONT S.P.A., Novara (IT)

(72) Inventors: Luigi Capuzzi, Novara (IT); Francesca Digioia, Barengo (IT); Giuseppina Carotenuto, Novara (IT)

(73) Assignee: NOVAMONT S.P.A., Novara (IT)

( * ) Notice: Subject to any disclaimer, the term of this patent is extended or adjusted under 35 U.S.C. 154(b) by 0 days.

(21) Appl. No.: 14/889,526

(22) PCT Filed: May 9, 2014

(86) PCT No.: PCT/EP2014/059538
§ 371 (c)(1),
(2) Date: Nov. 6, 2015

(87) PCT Pub. No.: WO2014/180979
PCT Pub. Date: Nov. 13, 2014

(65) Prior Publication Data
US 2016/0115142 A1    Apr. 28, 2016

(30) Foreign Application Priority Data
May 9, 2013   (IT) .............................. NO2013A0003

(51) Int. Cl.
*C07D 307/46*   (2006.01)

(52) U.S. Cl.
CPC ................................... *C07D 307/46* (2013.01)

(58) Field of Classification Search
CPC .................................................. C07D 307/46
See application file for complete search history.

(56) References Cited

FOREIGN PATENT DOCUMENTS

| CN | 101811066 A | 8/2010 |
| CN | 101906088 A | 12/2010 |
| JP | 2007 196174 A | 8/2007 |

OTHER PUBLICATIONS

Chareonlimkun, et al., Reactions of C5 and C6-sugars, cellulose, and lignocellulose under hot compressed water (HCW) in the presence of heterogeneous acid catalysts, Fuel 89, 2873-2880 (2010).*
International Search Report mailed by the International Searching Authority on Jun. 17, 2014 in International Application PCT/EP2014/059538 (4 pages).
Harishandra Jadhav et al. "Conversion of D-glucose into 5-hydroxymethylfurfural (HMF) using zeolite in [Bmim]Cl or tetrabutylammonium chloride (TBAC)/$CrCl_2$"; Tetrahedron Letters 53: 983-985 (2012).
Zhongshun Yuan et al. "Catalytic conversion of glucose to 5-hydroxymethyl furfural using inexpensive co-catalysts and solvents"; Carbohydrate Research 346: 2019-2023 (2011).
Fabio Carniato et al. "Ti-POSS covalently immobilized onto mesoporous silica: A model for active sites in heterogeneous catalytic epoxidation"; Inorganica Chimica Acta 380: 244-251 (2012).
Wei Zeng et al. "Catalytic Conversion of Glucose on Al—Zr Mixed Oxides in Hot Compressed Water"; Catal Lett 133: 221-226 (2009).
A. Chareonlimkun et al. "Reactions of $C_5$ and $C_6$-sugars, cellulose, and lignocellulose under hot compressed water (HCW) in the presence of heterogeneous acid catalysts"; Fuel 89: 2873-2880 (2010).
Per-Erik Tegehall "Synthesis of Crystalline Titanium (IV) Phosphates by Direct Precipitation from Ti(III) Solutions and Ion Exchange Properties of Some of the Prepared Phases"; Acta Chemica Scandinavica A 40: 507-514 (1986).
Fabio Carniato et al. "Titanosilsesquioxane Anchored on Mesoporous Silicas: a Novel Approach for the Preparation of Heterogeneous Catalysts for Selective Oxidations"; Chem. Eur. J. 14: 8098-8101 (2008).
Giulio Alberti et al. "Layered and Pillared Metal (IV) Phosphates and Phosphonates**"; Adv. Mater. 8, No. 4: 291-319 (1996).
Stephen Brunauer et al. "Adsorption of Gases in Multimolecular Layers"; the Bureau of Chemistry and Soils and George Washington University 60: 309-319 (1938).

* cited by examiner

*Primary Examiner* — Erich A Leeser
(74) *Attorney, Agent, or Firm* — Finnegan, Henderson, Farabow, Garrett & Dunner, LLP

(57) ABSTRACT

This invention relates to a process for the synthesis of 5-hydroxymethylfurfural (HMF) from saccharides. In particular this invention relates to a process for the dehydration of monosaccharides having 6 carbon atoms (hexoses), disaccharides, oligosaccharides, and polysaccharides to yield highly pure 5-hydroxymethylfurfural (HMF) in high yield.

20 Claims, 2 Drawing Sheets

Fig.1: schematic representation of the process.
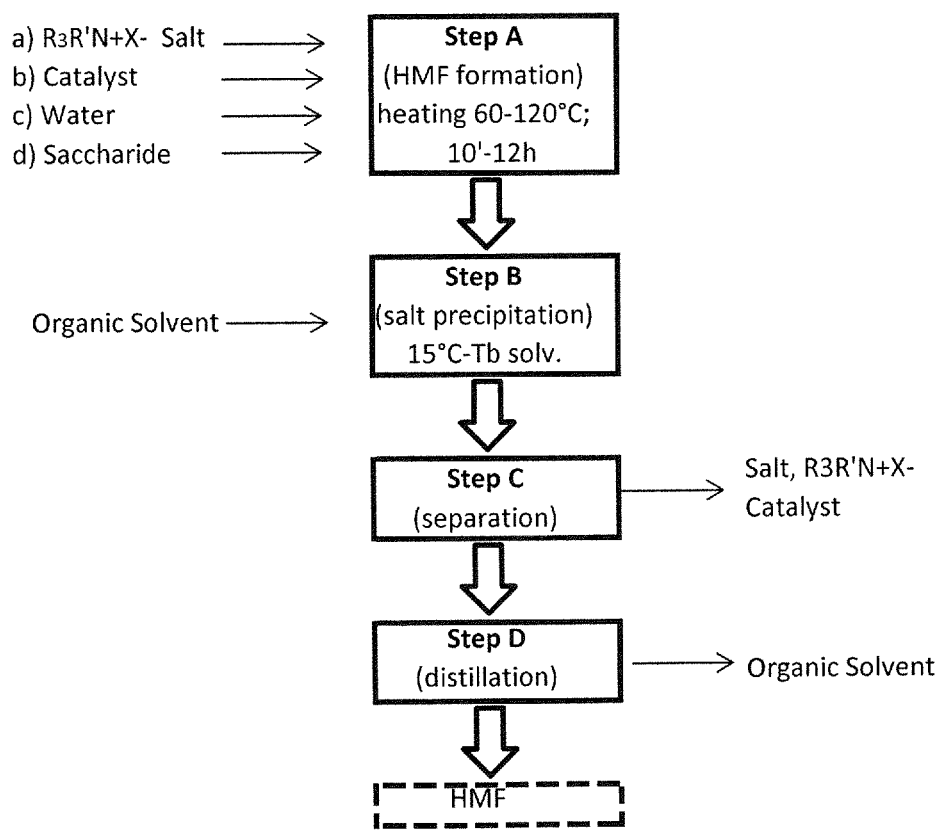

Fig. 2: schematic representation of the process with the recycle of ammonium salt/catalyst and organic solvent.
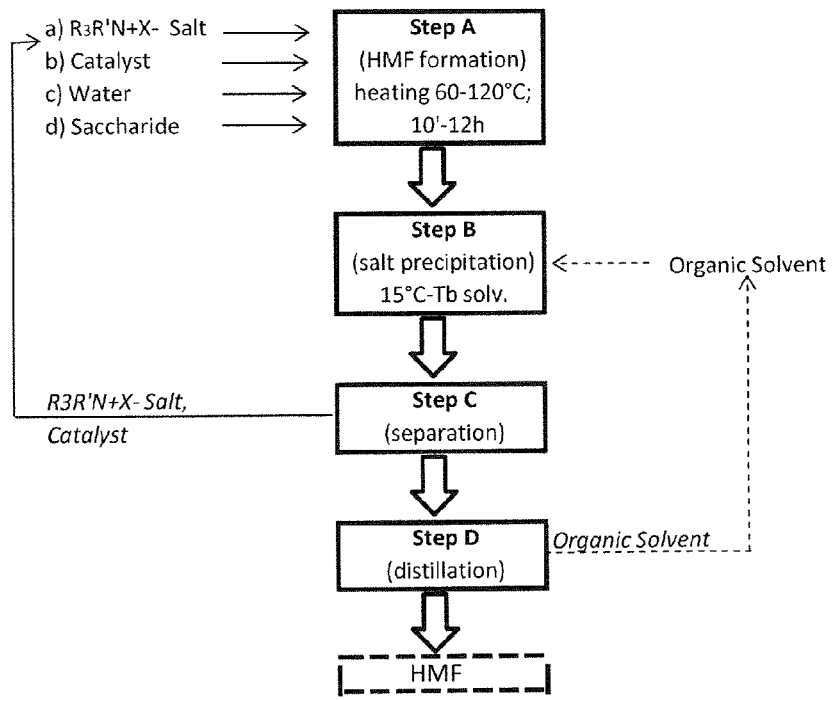

PROCESS FOR THE SYNTHESIS OF 5-HYDROXYMETHYLFURFURAL FROM SACCHARIDES

This application is a National Stage application under 35 U.S.C. §371 of International Application No. PCT/EP2014/059538, filed May 9, 2014, and claims the benefit of priority of Italian Application No. NO2013A000003, filed May 9, 2013, the content of each of which is incorporated herein by reference.

This invention relates to a new process for the synthesis of 5-hydroxymethylfurfural (HMF) from saccharides.

In particular this invention relates to a new process for the dehydration of monosaccharides having 6 carbon atoms (hexoses), disaccharides, oligosaccharides and polysaccharides deriving there from to yield highly pure 5-hydroxymethylfurfural (HMF) in high yield.

HMF is a product of significant importance for obtaining a whole series of useful intermediates—2,5-furandicarboxylic acid, 2,5-dimethylfuran, 2,5-(dihydroxymethyl) furan, etc.—from renewable sources.

The dehydration of monosaccharides having 6 carbon atoms, such as fructose and glucose, or disaccharides and polysaccharides deriving therefrom, such as saccharose and inulin, to yield HMF through the elimination of 3 molecules of water per monosaccharide unit is a reaction known in the literature:

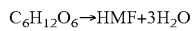

$$C_6H_{12}O_6 \rightarrow HMF + 3H_2O$$

The conversion may be performed in various types of solvents: water, aprotic dipolar solvents (for example dimethyl sulfoxide, N-methyl-2-pyrrolidone, N,N-dimethylformamide, N,N-dimethylacetamide), two-phase systems comprising water and organic solvents (for example 2-butanol, 4-methyl-2-pentanone), ionic liquids (for example N-methyl-2-pyrrolidone methylsulfonate, 1-ethyl-3-methylimidazolium chloride, 1-butyl-3-methylimidazolium chloride, 1-butyl-3-methylimidazolium tetrafluoroborate).

Various catalytic systems have been used to perform the conversion, such as for example acid catalysts of the mineral acids type, acid ion exchange resins, zeolites, supported heteropoly acids, and metal chlorides (for example $FeCl_3$, $CrCl_2$, $SnCl_4$). A strong acidity of the catalysts, as in the case of acid ion exchange resins, may nevertheless also favour the subsequent dehydration of HMF to levulinic and formic acids, or its oligomerisation or polymerisation to yield further by-products which contribute to lower the overall yield of the reaction.

While it is possible to obtain good conversions into HMF through the combination of some of these solvents and catalysts when using fructose as the starting substrate, because of the high solubility of HMF in water, its low melting point (30-34° C.) and its relative thermal instability it is still difficult to separate it from the reaction medium and by-products and to obtain it as an isolated highly pure product. For example the use of high boiling point water-soluble solvents such as dimethyl sulfoxide generally requires a separation by fractional distillation and subsequent column chromatography; the use of ionic liquids of the imidazolium, pyrrolidone and similar types, which are nevertheless costly and poorly compatible with the environment, generally require laborious extractions with organic solvents to separate out and recover the product from the ionic liquid.

In fact HMF yields reported in the literature are generally calculated by analysing the reaction mixtures (for example by HPLC) and are not determined on the basis of the quantity of product that has actually been isolated and purified.

Furthermore, when more abundant and more available saccharides than fructose, such as glucose, saccharose or inulin, are used as the starting substrate, HMF yields are appreciably lower. In fact, when glucose is used, a preliminary step of isomerisation to fructose is required in order to obtain the saccharide in the furanose configuration that is more suitable for forming HMF; when saccharose is used, a step of hydrolysis of the disaccharide and a partial isomerisation of the fraction constituting glucose are required; when inulin is used, a preliminary step of hydrolysis to fructose is required. Alkylammonium salts have also recently been proposed as catalysts or solvents for this type of reaction (CN 101906088; CN 101811066; Tetrahedron Letters 53, 2012, page 983-985; Carbohydrate Research 346, 2011, page 2019-2023), with HMF yields varying between 45 and 70% depending upon the starting saccharide.

In fact, despite the appreciable research activity dedicated to this specific reaction, the problem of obtaining highly pure HMF in high yields by the dehydration of saccharides through a process having a low environmental impact, which is easily implemented and economically sustainable, is still unsolved.

The applicant has now surprisingly found that it is possible to obtain high yields of high purity HMF through a new easily implemented and economically sustainable process starting from monosaccharides with 6 carbon atoms (hexoses), or disaccharides, oligosaccharides and polysaccharides formed from monosaccharide units having 6 carbon atoms, using a catalytic system comprising the combined use of a quaternary tetra-alkylammonium salt and specific catalysts selected from those specified below. A first object of this invention therefore comprises a process for the preparation of 5-hydroxymethylfurfural (HMF) comprising the steps of:

A) heating to a temperature of between 60 and 120° C., preferably between 80 and 110° C., for a time of between 10 minutes and 12 hours and optionally in a flow of inert gas, a mixture consisting of:
  a) a quaternary ammonium salt $R_3R'N^+X^-$, in which:
    R, which is the same or different, represents a $C_1$-$C_4$ alkyl group;
    R' represents a $C_1$-$C_{15}$ alkyl group;
    $X^-$ represents an anion selected from chloride, bromide, iodide, fluoride or hydroxide;
  b) at least one catalyst selected from:
    b-i) titanium (IV) oxide supported on silica having a specific surface area of between 150 and 900 $m^2/g$, preferably between 150 and 500 $m^2/g$, calcined at a temperature of between 150 and 900° C., preferably between 200 and 600° C.;
    b-ii) phosphotungstic acid, $H_3[P(W_3O_{10})_4]$, supported on silica having a specific surface area of between 150 and 900 $m^2/g$, preferably between 150 and 500 $m^2/g$, calcined at a temperature of between 150 and 900° C., preferably between 200 and 600° C.;
    b-iii) zirconium phosphate $Zr(HPO_4)_2$;
    b-iv) titanium phosphate $Ti(HPO_4)_2$;
  c) water in a quantity comprised between 1 and 50% by weight respect to the quaternary ammonium salt;
  d) one or more saccharides selected from monosaccharides having 6 carbon atoms, disaccharides, oligosaccharides and polysaccharides formed from monosaccharide units having 6 carbon atoms;

B) adding to the reaction mixture an organic solvent or a mixture of organic solvents in which the quaternary ammonium salt and the catalyst are highly insoluble and 5-hydroxymethylfurfural is soluble, at a temperature between 15° C. and the boiling point of the organic solvent or the mixture of organic solvents, obtaining the quaternary ammonium salt and the catalyst as solid phase, and the organic solvent or mixture of organic solvents and 5-hydroxymethylfurfural as liquid phase;

C) removing the solid phase from the liquid phase of step B); if necessary repeating stages B) and C) one or more times to complete separation of the 5-hydroxymethylfurfural from the quaternary ammonium salt and the catalyst;

D) separating off the organic solvent or mixture of organic solvents from the 5-hydroxymethylfurfural by distillation, preferably at a pressure below ambient pressure.

A further object of this invention is use of a mixture comprising:

a) a quaternary ammonium salt $R_3R'N^+X^-$, in which:
R, which is the same or different, represents a $C_1$-$C_4$ alkyl group;
R' represents a $C_1$-$C_{15}$ alkyl group;
$X^-$ represents an anion selected from chloride, bromide, iodide, fluoride or hydroxide;

b) at least one catalyst selected from:
b-i) titanium (IV) oxide, supported on silica having a specific surface area of between 150 and 900 $m^2/g$, preferably between 150 and 500 $m^2/g$, calcined at a temperature of between 150 and 900° C., preferably between 200 and 600° C.;
b-ii) phosphotungstic acid $H_3[P(W_3O_{10})_4]$, supported on silica having a specific surface area of between 150 and 900 $m^2/g$, preferably between 150 and 500 $m^2/g$, calcined at a temperature of between 150 and 900° C., preferably between 200 and 600° C.;
b-iii) zirconium phosphate $Zr(HPO_4)_2$;
b-iv) titanium phosphate $Ti(HPO_4)_2$;

c) water in a quantity of between 1 and 50% by weight with respect to the quaternary ammonium salt;

for the preparation of 5-hydroxymethylfurfural from one or more saccharides selected from monosaccharides having 6 carbon atoms or disaccharides, oligosaccharides and polysaccharides formed from monosaccharide units having 6 carbon atoms. Examples of saccharides which may be used to obtain HMF by dehydration according to the process according to this invention are monosaccharides such as fructose, glucose, galactose, mannose, disaccharides such as saccharose, maltose, lactose, cellobiose, oligosaccharides such as oligofructose containing 3-10 fructose units and polysaccharides such as fructan (e.g. inulin), starch, cellulose.

Specific examples of oligofructose are those having formula GFn, wherein G is the glucose unit, F is the fructose unit, n is the number of fructose units and is comprised between 3-10. A preferred example of fructan is inulin.

Fructose, glucose, saccharose, oligofructose, inulin and possible mixtures thereof are preferred as the starting saccharides. Examples of quaternary ammonium salts which can be used to perform the reaction according to the process according to this invention are tetramethylammonium chloride, tetraethylammonium chloride, tetrapropylammonium chloride, tetrabutylammonium chloride, tetramethylammonium bromide, tetraethylammonium bromide, tetrapropylammonium bromide, tetrabutylammonium bromide.

Preferred quaternary ammonium salts for carrying out the reaction according to this invention are chlorides and bromides, in particular tetramethylammonium chloride (TMAC), tetraethylammonium chloride (TEAC), tetraethylammonium bromide (TEAB), tetrabutylammonium bromide (TBAB).

Catalysts of type b-i) may be prepared from silica having the selected specific surface area and a solution of titanium isopropoxide in organic solvent (for example dioxan), separating the catalyst out by filtration and calcining at the desired temperature, or as reported for example in Inorganica Chimica Acta, 2012, 380, pages 244-251.

Preferred catalysts of type b-i) are those obtained from silica having a specific surface area of between 150 and 500 $m^2/g$ calcined at a temperature of between 200 and 600° C.

Catalysts of type b-ii) can be prepared by impregnating silica having the selected specific surface area with a solution of phosphotungstic acid in water, then removing the water at a temperature of 80-200° C. and calcining at the desired temperature. Those obtained from silica having a specific surface area of between 150 and 500 $m^2/g$ calcined at a temperature of between 200 and 600° C. are preferred.

The specific surface area of the catalysts b-i and b-ii prepared according to the present invention is preferably of between 100 and 350 $m^2/g$.

The specific surface area can be measured according to the BET method disclosed in S. Brunauer, P. H. Emmett and E. Teller, *J. Am. Chem. Soc,* 1938, 60, 309, measuring the amount of gas adsorbed on the surface of a material.

Depending on the value of specific surface area of the material, nitrogen or helium are used as gas.

The BET specific surface area of mesoporous materials (values of between 50-400 $m^2/g$) is herein measured by determining the amount of nitrogen adsorbed at 77 K and P/Po of approximately 0.3 and assuming a nitrogen cross sectional area of 16.2 $Å^2$, after degassing the catalyst sample at 100° C. overnight in vacuum at $10^{-6}$ Torr (about $0.13*10^{-3}$ Pa).

The BET specific surface area of microporous materials (values of between 400-1000 $m^2/g$) is herein measured by determining the amount of helium adsorbed at 4.2 K and P/Po of approximately 0.3 and assuming a helium cross sectional area of 1 $Å^2$, after degassing the catalyst sample at 100° C. overnight in vacuum at $10^{-6}$ Torr (about $0.13*10^{-3}$ Pa).

Catalysts of type b-iii) may be prepared as reported for example in Chemistry—A European Journal 2008, vol. 14, page 8098.

Catalysts of type b-iv) may be prepared as reported for example in Advanced Materials 1996, 8, 291-303 or in Acta Chem. Scand., 1986, A40, 507-514.

The ratio by weight between the saccharide and the quaternary ammonium salt is preferably from 1:100 to 2:1, more preferably from 1:10 to 1:1, even more preferably from 1:6 to 1:3.

The quantity of water is preferably between 1 and 50% by weight with respect to the quaternary ammonium salt, more preferably between 5 and 45%. The maintenance of a water content between 5 and 20% in the reaction mixture is preferred when monosaccharides and/or disaccharides are used, since it allows to limit the by-product formation.

The ratio by weight between the saccharide and the active phase of the catalysts is preferably from 500:1 to 1:1, more preferably from 400:1 to 1.3:1, even more preferably from 300:1 and 1.5:1, the expression "active phase" referring to the chemical species (on the inert support), able to promote the catalytic action.

When monosaccharides and/or disaccharides are used, the ratio by weight between the saccharide and the active phase of the catalysts of types b-i) and b-ii) may vary from 500:1 to 50:1, preferably between 400:1 and 80:1, more preferably between 300:1 and 90:1, whereas when using catalysts of types b-iii) and b-iv), the ratio by weight between the saccharide and the catalysts may vary from 100:1 and 1:1, preferably between 50:1 and 5:1, more preferably between 30:1 and 7:1.

When oligosaccharides and/or polysaccharides are used, the ratio by weight between the saccharide and the active phase of the catalysts of types b-i) and b-ii) may vary from 100:1 to 5:1, preferably between 50:1 and 7:1, more preferably between 30:1 and 10:1 whereas when using catalysts of types b-iii) and b-iv) the ratio by weight between the saccharide and the catalysts may vary from 100:1 and 1:1, preferably between 50:1 and 1.3:1, more preferably between 30:1 and 1.5:1.

FIG. 1 shows a schematic representation of the process of the invention.

FIG. 2 shows an embodiment of the process in which the ammonium salt and catalyst recovered in step C) are recycled to step A) and the organic solvent distilled in step D) is recycled to step B).

The dehydration reaction is performed during step A) by mixing the saccharide, the quaternary ammonium salt, the water and the catalyst and heating to a temperature between 60 and 120° C.

Although having a very high melting point (>250° C.), under the conditions used the quaternary ammonium salt acts as a solvent because it forms a eutectic with the saccharide which appreciably lowers the melting point of the reaction mixture and makes it possible to work in the liquid phase at a temperature ≥60° C., generally ≥80° C. Due to the formation of the eutectic, the presence of the quaternary ammonium salt allows to perform step A), under the conditions described, without the addition of organic solvents. The reaction is conveniently performed by first heating the solid mixture to the temperature and for the time required to obtain the saccharide and the quaternary ammonium salt in liquid phase and then heating the mixture with vigorous stirring to a temperature of between 60 and 120° C., preferably between 80 and 110° C., for the time required to complete the reaction at the desired yield. It should be considered that, in the present process, the excessive prolongation of the reaction can lead to the formation of by-products due to side reactions or decomposition of the product. Thus the reaction time, which is generally comprised between 10 minutes and 12 hours, preferably comprised between 15 minutes and 10 hours, and more preferably comprised between 20 minutes and 8 hours, may vary depending on the reaction conditions and on the saccharide used. For example, when monosaccharides and/or disaccharides are used, the reaction time is preferably comprised between 10 minutes and 2 hours, whereas when oligosaccharides and/or polysaccharides are used, it is preferably comprised between 1 hour and 6 hours.

At the end of the reaction an organic solvent or a mixture of organic solvents in which the quaternary ammonium salt and the catalyst are highly insoluble and 5-hydroxymethylfurfural is soluble is added to the mixture, holding the mixture within the temperature range of 15° C. to the boiling point of the organic solvent or mixture of organic solvents for the time required to achieve precipitation of the ammonium salt and the catalyst, and dissolution of the HMF (step B).

The organic solvents used in step B) of the present process are those in which the solubility of the quaternary ammonium salt and of the catalyst is low, generally less than 20 g/l at 20° C. and the solubility of HMF is high, generally higher than 100 g/l at 20° C. Examples of suitable organic solvents for precipitation of the quaternary salt and catalyst are esters (e.g. ethyl acetate, butyl acetate, isopropyl acetate), ketones (e.g. 2-butanone and 4-methyl-2-pentanone), ethers (e.g. tetrahydrofuran), or halogenated alkanes (e.g. chloroform). A list of their boiling points ($T_{eb}$) is given in the table below:

| Organic Solvent | $T_{eb}$ (° C.) |
|---|---|
| ethyl acetate | 77 |
| isopropyl acetate | 102 |
| butyl acetate | 127 |
| 2-butanone | 79.6 |
| 4-methyl-2-pentanone | 116 |
| tetrahydrofuran | 66 |
| chloroform | 61 |

Thus for instance, step B is performed holding the mixture within the temperature range of 15° C.-77° C. when ethyl acetate is used as organic solvent, of 15° C.-79.6° C. when 2-butanone is used as organic solvent, of 15° C.-66° C. when tetrahydrofuran is used as organic solvent, or of 15° C.-61° C. when chloroform is used as organic solvent.

Preferably, step B is performed holding the mixture within a temperature range of 15° C.-130° C.; advantageously, the temperature range is of 20° C.-80° C.

In order to facilitate the precipitation, optionally at this stage the water is at least partially removed from the mixture, for example by distillation, preferably under vacuum. When an organic solvent forming an azeotrope with water (e.g. 2-butanone) is used, water is advantageously removed via azeotropic distillation.

According to an advantageous embodiment, the reaction mixture is diluted hot with a limited amount of an organic solvent in which the quaternary ammonium salt is soluble, for example alcohols such as ethanol, 1-butanol, 2-butanol, isopropyl alcohol, generally ethanol; a solvent or a mixture of organic solvents in which the quaternary ammonium salt and the catalyst are both insoluble is then added and these precipitate out as solids which are separated off by filtration (step C). The 5-hydroxymethylfurfural instead remains dissolved in the organic phase, from which it can easily be recovered by distillation of the solvent or mixture of solvents, preferably at reduced pressure (step D).

Examples of preferred organic solvents are 2-butanone, ethyl acetate, tetrahydrofuran and chloroform.

Alternatively, according to another embodiment, at the end of the reaction the mixture is directly treated when hot and with vigorous stirring with an organic solvent or a mixture of organic solvents in which the quaternary ammonium salt and the catalyst are insoluble and in which HMF and, at least partly, water are instead soluble.

The organic phase is separated off from the ammonium salt and the catalyst (step C), for example by settling or filtration, and the solvent is removed by distillation, preferably at reduced pressure, to obtain the HMF (step D). Preferred solvents for this operation are tetrahydrofuran (together with chloroform for example for the precipitation of chloride ammonium salts such as TEAC) and 2-butanone (for example for the precipitation of bromide ammonium salts such as TEAB).

The operations of steps B), C) and D) may be repeated several times, possibly even in a continuous extraction system.

The water forming in the course of the reaction (during step A) may be removed from the reaction system by a flow of inert gas, preferably nitrogen, and possibly under vacuum; the residual water, if present, is finally separated from the HMF at the end of step D) by distillation together with the organic solvent or mixture of organic solvents, preferably at reduced pressure.

The organic solvent separated from HMF during step D) may be advantageously reused (after removal of the water, for example by distillation) and reused to perform step B) in successive batches.

The solid phase recovered at the end of step C), comprising the quaternary ammonium salt and the catalyst, can be reused several times to perform the reaction of step A) in successive batches without substantial loss of efficiency in the catalytic system. The process of the present invention can also be performed continuously or semi-continuously.

As mentioned, because of the special characteristics of the catalytic system identified, through the process according to this invention it is possible to obtain highly pure HMF in high yield.

The catalysts used are in fact bifunctional heterogeneous acids, which are characterised by the concomitant presence of Bronsted and Lewis acid sites.

This allows to achieve high conversion of the saccharide because of the presence of Bronsted type acid sites, and greater selectivity for HMF because of the presence of Lewis acid type sites.

The use of quaternary ammonium salts as solvents represents a further advantage of this invention; in addition to being non-toxic and eco-compatible, they can be easily recovered from the reaction environment by dilution with organic solvents and crystallisation, which makes it possible to reuse them in subsequent runs of the process. Because of their ionic conductibility characteristics they act as phase transfer agents, further catalysing the conversion of saccharide into HMF.

The following examples, which are to be regarded as being illustrative and not restrictive of the invention, are provided now in order to better illustrate it.

EXAMPLES

BET Specific Surface Area Determination

The specific surface area was estimated using a Sorptomatic 1990 Thermo Finningen instrument. After the sample (0.35 g), which was previously degassed at 100° C. overnight in vacuum at $10^{-6}$ Torr (about $0.13*10^{-3}$ Pa), was cooled at 77 K, $N_2$ gas at the specified volume of 17.20 cm$^3$ (considering 0.25 cm$^3$ of dead volume of piston) was introduced until the achievement of the saturation pressure of 720 Torr (about $9.6*10^4$ Pa). The total volume of introduced nitrogen gas was of about 130-150 cm$^3$. The constant pressure showing equilibrium of adsorption was observed after 3 h 52' from $N_2$ introduction.

Characterization of the Product

After removal of the solvent (concentration) from the liquid phase at the end of step D of the process, the product was left in a stream of nitrogen for 12 h in order to remove any traces of organic solvent and water, and then was weighed.

A sample (1 mg) was dissolved in 1 ml of 0.005N $H_2SO_4$ solution and filtered through teflon filters (pore diameter: 0.20 μm) and then analyzed by HPLC using a reference standard in order to determine the purity of HMF.

HPLC analysis have been performed on a chromatograph equipped with RI detector and a Rezex ROA-Organic acid H+ (8%) 300×7.8 mm column. A 0.005N $H_2SO_4$ solution at a flow rate of 0.6 mL/min was used as eluent. The column temperature was set at 65° C.

Example 1

Preparation of the Catalyst b-ii (HPWO/Si$_{500}$)

A solution of 1.0 g or 3.0 g of phosphotungstic acid in 11 ml of distilled water was used to uniformly impregnate 10 g of commercial silica (Aerolyst 3038, Degussa: specific surface area 180 m$^2$/g), to obtain respectively 10%$_{wt}$ HPWO/Si$_{500}$ and 30%$_{wt}$ HPWO/Si$_{500}$.

The paste was first dried in a stove at 80° C. for 12 hours and then calcined at 200° C. for 2 hours. A blue/purple colour powder formed; this was then treated at 200° C. for 2 hours and finally for a further 2 hours at 500° C. until a yellow powder was formed.

The 10%$_{wt}$ HPWO/Si$_{500}$ catalyst so prepared (having a BET specific surface area of 159 m$_2$/g), has been used for the reactions in Examples 4, 5 and 9.

Example 2

Preparation of the Catalyst b-i (Ti/Si$_{500}$)

The following were placed in a 250 ml glass flask in an atmosphere of nitrogen:
 100 ml of dioxan;
 6 g of silica (Aerolyst 3038, Degussa: specific surface area 180 m$^2$/g);
 0.88 g of titanium isopropoxide [Ti(i-PrO)$_4$].

These were kept stirred at ambient temperature for 5 hours.

The solid was then filtered out, washed with dioxan, dried in a stove at 120° C. for 12 hours, calcined at 200° C. for 2 hours and then at 500° C. for 2 hours.

The Ti/Si$_{500}$ catalyst so prepared (having a BET specific surface area of 170 m$^2$/g) has been used for the test in Example 6.

Example 3

Preparation of the Catalyst b-iii (Zr(HPO$_4$)$_2$)

3.3 mmol of zirconyl propionate (Goldmann Gmbh) were dissolved in 10 ml anhydrous ethanol.

1.35 ml of phosphoric acid (85%) were added to the ethanol solution under stirring at ambient temperature. A clear solution was obtained which, within a few minutes, turned into gel. The obtained gel was washed three times with ethanol to remove the excess of phosphoric acid and co-products such as propionic acid. The gel was dried in a stove at 60° C. for 24 hours.

Example 4

Dehydration of Saccharose

The following were placed in a 50 ml glass flask:
 2 g of saccharose;
 0.2 g of 10% HPWO/Si$_{500}$ catalyst prepared in Example 1;
 10 g of tetraethylammonium bromide (TEAB);
 1 g of distilled water.

The reaction mixture was raised to a temperature of 80° C. and stirred for 15 minutes; the temperature was then raised to 100° C. over about 15 minutes and vigorous stirring was maintained for 60 minutes, removing the water formed by the reaction with a flow of nitrogen.

At the end of the reaction the mixture was treated with 50 ml 2-butanone with vigorous stirring. The solvent was decanted and removed under vacuum, heating to 80° C.

100 ml 2-butanone was added to the reaction residue and heated under reflux for approximately 10 minutes; the operation of extracting the ammonium salt was repeated three times. Finally the organic solution was filtered off to remove the solid phase and the liquid phase was concentrated at reduced pressure. 1.05 g of HMF with a purity of 94.1% was obtained, in a yield of 67%.

Example 5

Dehydration of Glucose/Fructose Syrup

The following were placed in a 50 ml glass flask:
2.83 g of maize syrup containing 2.17 g of a 1:1 glucose/fructose mixture and 0.66 g of water;
0.2 g of 10% HPWO/$Si_{500}$ catalyst prepared in Example 1;
10 g of tetraethylammonium bromide (TEAB);
0.3 ml of distilled water.

The reaction mixture was raised to the temperature of 80° C. and kept stirred for 15 minutes; the temperature was then raised to 100° C. over approximately 15 minutes and vigorous stirring was maintained for 60 minutes, removing the water formed by the reaction in a flow of nitrogen.

Finally the mixture was diluted with approximately 4 ml of hot ethanol (60° C.) and the salt was precipitated out by adding ethyl acetate. The organic phase was filtered to separate out the ammonium salt and the catalyst as a solid phase, then the liquid phase was filtered on silica gel (pore diameter 60 Angstrom) and concentrated at reduced pressure; 1.28 g of HMF with a purity of 88.6% was obtained in a yield of 75%.

Example 6

Dehydration of Fructose

The following were placed in a 50 ml glass flask:
2.1 g of fructose;
0.2 g of Ti/$Si_{500}$ catalyst prepared in Example 2;
9.1 g of tetraethylammonium chloride (TEAC);
0.9 ml of distilled water.

The reaction mixture was raised to the temperature of 80° C. and kept stirred for 15 minutes; the temperature was then raised to 100° C. over approximately 15 minutes and vigorous stirring was maintained for a further 15 minutes. Finally the mixture was dissolved in ethanol (10 ml) at a temperature of approximately 70-75° C.; the ethanol and the water were removed under reduced pressure at a temperature of 70-75° C. The residue was then dissolved again in chloroform, tetrahydrofuran was added and the ammonium salt precipitated out and was recovered by filtration together with the catalyst. The liquid phase was filtered on silica gel and concentrated at reduced pressure; 1.4 g of HMF with a purity of 97.6% was obtained in a yield of 93%.

The recovered solid phase containing ammonium salt and catalyst was subsequently reused to perform fructose dehydration with the same procedure. After the third recycle 1.25 g of HMF (corresponding to a reaction yield of about 82%) was obtained.

Example 7

Comparative

The same reaction of Example 6 was carried out without the addition of a catalyst. After precipitation of the ammonium salt, the liquid phase, mainly consisting of chloroform and THF, contained a quantity of HMF corresponding to a yield of merely 5%.

Example 8

Dehydration of Fructose

The following were placed in a 50 ml glass flask:
2.13 g of fructose;
0.2 g of titanium phosphate Ti($HPO_4$)$_2$;
10 g of tetraethylammonium bromide (TEAB);
1 g of distilled water.

The reaction was carried out as in Example 4. A 80% yield of HMF (purity of 99.6%) was obtained.

Example 9

Recycling of Solid Phase

The following were placed in a 50 ml glass flask:
2 g of fructose;
0.2 g of 10% HPWO/$Si_{500}$ catalyst prepared in Example 1;
10 g of tetraethylammonium bromide (TEAB);
0.91 ml of distilled water.

The reaction mixture was raised to the temperature of 80° C. and kept stirred for 15 minutes; the temperature was then raised to 100° C. over approximately 15 minutes and vigorous stirring was maintained for a further 15 minutes.

Finally 10 ml ethanol was added and then removed along with the water via azeotropic distillation. 200 ml ethyl acetate were then added to precipitate the ammonium salt. The organic phase containing HMF was separated by filtration from the solid phase.

2 g of fructose and 0.91 ml of water were added to the solid phase containing the ammonium salt and catalyst and the reaction and extraction procedure above described were repeated. The recycling of the solid phase was repeated other 6 times with the same procedure; the results (HMF yields) obtained after each solid phase use are reported in the table below.

| TEAB - HPWO/$Si_{500}$ | HMF yield (%) |
| --- | --- |
| 1st run | 95.4 |
| 1$^{st}$ recycle | 93.4 |
| 2$^{nd}$ recycle | 89.8 |
| 3$^{rd}$ recycle | 80.1 |
| 4$^{th}$ recycle | 75.1 |
| 5$^{th}$ recycle | 74.9 |
| 6$^{th}$ recycle | 74.8 |
| 7$^{th}$ recycle | 74.2 |

Example 10

Dehydration of Fructose

The following were placed in a 50 ml glass flask:
1.97 g of fructose;
0.2 g of Zyrconium phosphate (α-Zr($HPO_4$)$_2$) prepared in Example 3;
10 g of tetraethylammonium bromide (TEAB);
0.91 ml of distilled water.

The reaction was carried out as in Example 4.

At the end of the reaction the mixture was treated with 50 ml 2-butanone and water was removed under vacuum. 200 ml 2-butanone was added to the reaction residue to extract HMF. The organic solution containing HMF was filtered off to separate the ammonium salt and catalyst as solid phase and finally the organic solvent was distilled off from the liquid phase. 1.22 g of HMF with a purity of 99% was obtained, corresponding to a yield of 87.6%.

Example 11

Hydrolysis and Dehydration of Inulin

The following were placed in a 50 ml glass flask:
2 g of inulin;
0.33 g of 30% HPWO/Si$_{500}$ prepared in Example 1;
10 g of tetraethylammonium bromide (TEAB);
4 ml of distilled water.

The reaction mixture was raised to a temperature of 80° C. and stirred for 15 minutes; the temperature was then raised to 110° C. over about 120 minutes and vigorous stirring was maintained for 120 minutes, removing the water formed by the reaction with a flow of nitrogen.

At the end of the reaction the mixture was treated with ethanol and water was removed under vacuum. 250 ml ethyl acetate was added to the reaction residue to extract HMF. The organic solution containing HMF was filtered off to separate the ammonium salt and catalyst and finally the organic solvent was distilled off. 1.20 g of HMF (corresponding to a yield of 66.3%) was obtained.

The invention claimed is:

1. A process for preparing 5-hydroxymethylfurfural comprising the steps of:
   A) heating at a temperature from 60° C. to 120° C. for a time from 10 minutes to 12 hours a reaction mixture consisting of:
      a) a quaternary ammonium salt $R_3R'N^+X^-$ wherein:
         R, which is the same or different, is a $C_1$-$C_4$ alkyl group;
         R' is a $C_1$-$C_{15}$ alkyl group;
         $X^-$ is an anion selected from chloride, bromide, iodide, fluoride, and hydroxide;
      b) at least one catalyst selected from:
         b-i) titanium (IV) oxide supported on silica having a surface area from 150 m$^2$/g to 900 m$^2$/g, calcined at a temperature from 150° C. to 900° C.;
         b-ii) phosphotungstic acid, $H_3[P(W_3O_{10})_4]$, supported on silica having a surface area from 150 m$^2$/g to 900 m$^2$/g, calcined at a temperature of from 150° C. to 900° C.;
         b-iii) zirconium phosphate $Zr(HPO_4)_2$; and
         b-iv) titanium phosphate $Ti(HPO_4)_2$;
      c) water in a quantity from 1% by weight to 50% by weight with respect to the quaternary ammonium salt;
      d) a saccharide selected from a monosaccharide having 6 carbon atoms, and a disaccharide, oligosaccharide, and polysaccharide formed from a monosaccharide unit having 6 carbon atoms;
   B) adding to the reaction mixture an organic solvent or a mixture of organic solvents in which the quaternary ammonium salt and the catalyst are highly insoluble and 5-hydroxymethylfurfural is soluble, at a temperature from 15° C. to the boiling point of the organic solvent or of the mixture of organic solvents, obtaining the quaternary ammonium salt and the catalyst as solid phase, and the organic solvent or mixture of organic solvents and 5-hydroxymethylfurfural as liquid phase;
   C) removing the solid phase from the liquid phase of step B);
   D) separating off the organic solvent or mixture of organic solvents from the 5-hydroxymethylfurfural by distillation.

2. The process according to claim 1, wherein B) and C) are repeated one or more times.

3. The process according to claim 1, wherein the saccharide in D) is selected from fructose, glucose, saccharose, oligofructose, inulin and mixtures thereof.

4. The process according to claim 1, wherein $X^-$ is chloride or bromide.

5. The process according to claim 1, wherein the quaternary ammonium salt is selected from tetramethylammonium chloride, tetraethylammonium chloride, tetraethylammonium bromide, and tetrabutylammonium bromide.

6. The process according to claim 1, wherein the catalyst is titanium (IV) oxide, supported on silica having a surface area from 150 m$^2$/g to 900 m$^2$/g calcined at a temperature from 150° C. to 900° C.

7. The process according to claim 6, wherein the catalyst titanium (IV) oxide is supported on silica having a surface area from 150 m$^2$/g to 500 m$^2$/g calcined at a temperature from 200° C. to 600° C.

8. The process according to claim 6, wherein the catalyst has a surface area from 100 m$^2$/g to 350 m$^2$/g.

9. The process according to claim 1, wherein the catalyst is phosphotungstic acid, $H_3[P(W_3O_{10})_4]$, supported on silica having a surface area from 150 m$^2$/g to 900 m$^2$/g calcined at a temperature from 150° C. and 900° C.

10. The process according to claim 9, wherein the catalyst $H_3[P(W_3O_{10})_4]$ is supported on silica having a surface area from 150 m$^2$/g and 500 m$^2$/g calcined at a temperature from 200° C. to 600° C.

11. The process according to claim 9, wherein the catalyst has a surface area from 100 m$^2$/g to 350 m$^2$/g.

12. The process according to claim 1 wherein the catalyst is zirconium phosphate $Zr(HPO_4)_2$.

13. The process according to claim 1, wherein the catalyst is titanium phosphate $Ti(HPO_4)_2$.

14. The process according to claim 1, wherein the saccharide is selected from monosaccharides and/or disaccharides and the quantity of water in step A) is from 5% by weight to 15% by weight with respect to the quaternary ammonium salt.

15. The process according to claim 1, wherein the organic solvent of step B) is selected from ethyl acetate, butyl acetate, isopropyl acetate, 2-butanone, 4-methyl-2-pentanone, tetrahydrofuran, chloroform and mixtures thereof.

16. The process according to claim 1, wherein the time of step A) is from 15 minutes to 10 hours.

17. The process according to claim 1, wherein the time of step A) is from 20 minutes to 8 hours.

18. The process according to claim 1 wherein the saccharide is selected from monosaccharides and/or disaccharides and the time of step A) is from 10 minutes to 2 hours.

19. The process according to claim 1, wherein the saccharide is selected from oligosaccharides and/or polysaccharides and the time of step A) is from 1 hour to 6 hours.

20. The process according to claim 1, wherein the ratio by weight between the saccharide and the active phase of the catalysts in step A) is from 500:1 to 1:1.

* * * * *